United States Patent [19]

Li

[11] 4,294,993
[45] Oct. 13, 1981

[54] PURIFICATION OF BISPHENOL-A

[75] Inventor: Ming K. Li, Schenectady, N.Y.

[73] Assignee: General Electric Company, Schenectady, N.Y.

[21] Appl. No.: 139,969

[22] Filed: Apr. 14, 1980

[51] Int. Cl.³ ............................................. C07C 37/70
[52] U.S. Cl. .................................... 568/724; 568/749
[58] Field of Search ............................... 568/749, 724

[56] References Cited

U.S. PATENT DOCUMENTS

| | | | |
|---|---|---|---|
| 2,791,616 | 5/1957 | Luten | 568/724 |
| 2,959,622 | 11/1960 | Grimme et al. | 568/724 |
| 3,073,868 | 1/1963 | Prahl et al. | 568/724 W |
| 3,673,262 | 6/1972 | Prahl et al. | 568/724 |
| 4,156,089 | 5/1979 | Li | 568/724 |
| 4,212,997 | 7/1980 | Adam | 568/724 |

*Primary Examiner*—Werren B. Lone
*Attorney, Agent, or Firm*—Joseph T. Cohen; James C. Davis, Jr.

[57] ABSTRACT

Pure bisphenol-A can be obtained by treating the adduct of the latter and phenol with either toluene or a mixture of toluene and water.

5 Claims, No Drawings

PURIFICATION OF BISPHENOL-A

This invention is concerned with the purification of 2,2-bis(4-hydroxyphenyl) propane (hereinafter identified as "bisphenol-A" or "BPA"). More particularly, the invention is directed to a method for recovering bisphenol-A in a purified state from a mixture of the latter and impurities derived from the acid-catalyzed condensation of phenol and acetone, which method comprises (1) intimately admixing a mixture of (a) a preformed isolated adduct of phenol and the above-identified dihydroxydiphenyl propane and (b) impurities associated with (a), with sufficient toluene or a mixture of toluene and water to form a homogeneous solution when the mixture is heated at 45° to 110° C., and (2) cooling the solution to a temperature where purified BPA precipitates in a highly purified state substantially free of phenol and impurities which originally were present with the adduct.

Bisphenol-A is commercially prepared by reacting phenol and acetone in the presence of an acidic material such as sulfuric acid, hydrochloric acid, cation exchange resins, etc. As a result of carrying out this reaction, the bisphenol-A produced is accompanied by undesirable impurities such as the 2-(4-hydroxyphenyl)-2-(2-hydroxyphenyl)propane (hereinafter identified as "o,p-isomer") having the formula

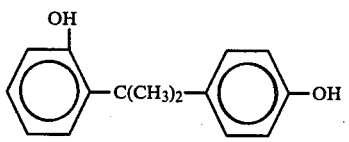

as well as other impurities including phenol itself used in making the bisphenol-A, a trishydroxyphenyl compound of the formula

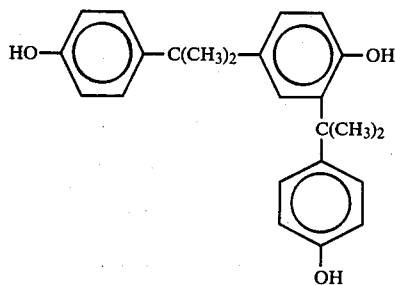

(hereinafter identified as "BPX-1"), small amounts of other impurities such as the two compounds having the formulas

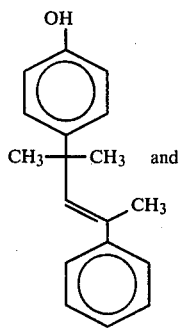 and

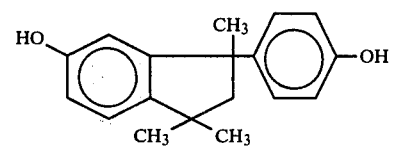

(hereinafter identified as "LD/CD"), etc.

Since bisphenol-A is used in making polycarbonate resins by reaction of the latter with either phosgene or diphenyl carbonate, or for making epoxy resins, both resins being used extensively in commercial applications involving molding, casting, and sheet forming purposes, it is highly important that the monomeric bisphenol-A used to make such resins be as pure as possible in order to avoid adverse effects on the properties of the polymers thus obtained.

The preparation of the bisphenol-A by the reaction of phenol and acetone is usually carried out in excess phenol (>2 moles phenol per mole acetone). Upon sufficient cooling of the reaction product mixture, an adduct in which there is 1 mole of phenol per mole of bisphenol-A will crystallize out of the aforesaid product mixture. The isolated product, which is in a fairly pure state represents a starting point of making bisphenol-A of high purity.

One method for working with this adduct to arrive at a purified bisphenol-A is described in Luten U.S. Pat. No. 2,791,616 issued May 7, 1957. According to this patent, the adduct obtained as a result of carrying out the initial reaction in the presence of the acidic condensation catalyst, uses a large excess of water within a well-defined temperature range which serves to liberate the phenol from the adduct with the result that most of the phenol is dissolved in the water while substantially all the bisphenol-A remains behind in the solid state. However, this process suffers from several disadvantages. Excessive amounts of water are usually required. Also the water obtained containing the phenol, whether liberated from the adduct or the excess amount used in carrying out the initial condensation reaction, is in the form of a mixture which requires considerable processing and expenditure of energy in order to recover the phenol so that it can be used again for reaction with the acetone.

Another purification processing technique which has been employed after the adduct is broken is to subject the bisphenol-A to high temperature distillation to separate the latter from the impurities. In the process of using the high temperatures required (even under vacuum conditions) some of the PBA is lost through degradation and tar formation, thus contributing to a process which does not permit optimum yields of the bisphenol-A in a highly purified state.

Unexpectedly, I have discovered that I can treat the bisphenol-A adduct with toluene alone or with a mixture of toluene and water, to form a homogeneous solution or a liquid-liquid mixture, respectively, at elevated temperatures whereby the toluene ingredient has been found capable of breaking the adduct thereby causing solution of the impurities in the toluene or toluene-water mixture and the release of phenol either from the adduct or the residual phenol remaining from the reaction to make the bisphenol-A. The resulting solution or liquid-liquid mixture can be cooled to precipitate solid bisphenol-A in a highly purified state, with the bisphenol-A in the form of larger than normal crystals, thus facilitating more ready and more complete recovery of the purified BPA. The liquid phase (or phases), depending on whether toluene alone or a toluene-water combination is used, contains the impurities and phenol originally present as excess or in the phenol-bisphenol-A adduct.

The initial treatment of the BPA-phenol adduct is carried out with an amount of toluene, which on a weight basis, is equal to from 0.5 to 10 parts toluene per part of the adduct. When a mixture of water and toluene is used in combination with the adduct, the amount of toluene in such a mixture should be within the range recited above where only toluene is employed. The water which is used with the toluene can however be varied widely and on a weight basis, advantageously ranges from about 0.1 to 4 parts of water per part of toluene used. The amount of toluene or the mixture of toluene and water will to some extent be determined by (1) the temperature at which a homogeneous solution or a liquid-liquid mixture is obtained and (2) the desire to utilize the maximum capacity of the reaction vessel in which the toluene or toluene-water mixture is used with the adduct.

The temperature at which the mixture of the adduct and either the toluene or toluene-water combination is heated to form a homogeneous toluene solution or a liquid-liquid mixture (where toluene and a sufficient amount of water is used) can be varied widely depending upon the amount of toluene or water present, the degree of excess phenol or impurities present, etc. Although generally temperatures of above 75°–125° can be employed, I have found that generally temperatures in the range of from about 85°–110° are satisfactory for the purposes. When water is used in combination with the toluene, lower temperatures can be used and I have found that in those instances where a sufficient amount of water and toluene is used in combination with the bisphenol-A-phenol adduct, temperatures as low as 45°–65° C. can be employed to form a liquid liquid mixture, which is required before precipitating the purified BPA.

In those instances where the requisite amount of water is used with the toluene, precipitated purified crystals of BPA are readily attained upon reduction of the temperature to around 20°–35° C. from the liquid-liquid mixture. It should be recognized that although good yields of bisphenol-A are realized by means of the present invention, additional yields of bisphenol-A can be realized by further treatment of the isolated toluene or even of the isolated aqueous phase by further cooling to lower temperatures, and then collecting the additional crop of bisphenol-A crystals, thereby enhancing the yield of the desired purified bisphenol-A.

Although the bisphenol-A crystals obtained as a result of practicing my above-described invention are in a highly purified state, it is possible that there still may be some residual impurities present, which although they may not be detrimental to polymers made with the bisphenol-A, still, anticipating room for improvement in properties of such polymers, these crystals can be washed with either methylene chloride (as is described in my U.S. Pat. No. 4,156,098) or additional amounts of toluene, and thereafter dried to obtain a bisphenol-A which is exceptionally pure approaching 100% purity. When these highly purified bisphenol-A crystals are used to make, for instance, polycarbonate resins, it will be found that the color properties of the polycarbonate resins are almost water-white thus pointing to possible expansion of uses of such resins in applications where color might be a detriment.

My invention has major advantages over the process described in the above-mentioned Luten U.S. Pat. No. 2,791,616. Luten employs amounts of water for addition to the adduct which are quite large and which increase the complexity of the processing techniques and the isolation of the purified bisphenol-A. In addition, by heating the mixture of the toluene and toluene-water mixture with the adduct at elevated temperatures as is done in my invention, the adduct is broken more readily so that the phenol thus liberated can be removed more efficiently and more rapidly by passages of phenol either into the toluene or into the aqueous phase when the toluene-water system is used.

The term "bisphenol-A phenol adduct" is used herein is intended to mean either (1) the adduct which is obtained as a result of the reaction of the phenol and the acetone in the presence of an acidic condensation catalyst, as well as (2) a preformed adduct which is made from impure bisphenol-A which has been treated with a sufficient amount of phenol to form the adduct. The molar concentration of the adduct consists of 1 mole of the bisphenol-A and 1 mole of phenol, and, on a weight basis, represents approximately 70 percent of the bisphenol-A and 30 percent phenol.

In order that those skilled in the art may better understand how the present invention may be practiced, the following examples are given by way of illustration and not by way of limitation. Unless otherwise indicated, all parts are by weight. Stirring was used to effect mixing of the adduct and the toluene or toluene-water mixture.

The bisphenol-A adduct used in the following examples can be prepared in various ways. One example of such preparation is as follows:

EXAMPLE 1

Crude bisphenol-A (obtained from the reaction of phenol and acetone in the presence of an acidic catalyst, such as $H_2SO_4$) is dissolved with stirring in a large excess of phenol at a temperature of about 95° C. The adduct which precipitates is removed from the mother liquor consisting mostly of phenol and impurities. This procedure allows for a close simulation of the adduct that would be obtained in a bisphenol-A manufacturing plant.

EXAMPLE 2

To a reaction vessel equipped with stirring means and a condenser, were added 25.01 grams of the above-identified BPA-phenol adduct and 54.64 grams of toluene. The mixture was stirred and heated to a temperature of about 95° C. at which point the mixture of ingredients became a homogeneous solution. The heated solution was then cooled at the rate of about 1° C./3.5 min. until the temperature reached 50° C., at which point the BPA crystallized from the solution. The slurry thus obtained was transferred to a Buchner funnel, the temperature of which was controlled at around 50° C. and the liquid (mother liquor) was filtered from the solid material to yield 14.01 grams of precipitated purified bisphenol-A crystals. These crystals were slurried with two parts toluene (by weight, about 28 grams) per part crystals, the liquid toluene filtered off and the solid crystals of BPA again rinsed with two parts toluene, by weight, to give 13.02 grams of pure BPA having a melting point of 155.5° C.±0.5° C. Analysis of the product thus obtained compared with the original starting adduct and the impurities therein is shown below in Table I.

TABLE I

|  | % BPA | % Phenol | % o,p-Isomer | % L.D./C.D. | % BPX-I | Recovery Based on % BPA |
|---|---|---|---|---|---|---|
| Adduct | 67.785 | 31.888 | 0.217 | 0.075 | 0.035 | — |
| Purified Product | ~100.0 | — | — | — | — | 76.80 |

EXAMPLE 3

Example 2 was repeated with the exception that 14.93 grams of the adduct and 59.72 grams of toluene were employed. Because of the higher weight ratio of toluene to adduct, the homogeneous solution was observed to have formed at about 89.5° C. The solution was cooled to crystallize the BPA from the solution and 8.85 grams of purified BPA crystals was collected. Again, this solid was slurried with 7.17 grams of toluene for about 5 minutes and the toluene was filtered and the residue dried to give a yield of 8.37 grams of highly purified BPA, the melting point which was about 155° C. Analysis of the purified product showed that the bisphenol-A obtained in accordance with this example was 99.108% pure BPA but contained 0.892% phenol. The percent recovery of purified bisphenol-A based on the theoretical amount was 81.97%.

EXAMPLE 4

In this example, 300.1 grams of the adduct and 1200 grams of toluene were mixed together and heated until a homogeneous solution was formed at about 91° C. The system was slowly cooled to 40.5° C. while maintaining good mixing and some seed crystals of bisphenol-A were supplied to induce crystallization. The slurry thus obtained was centrifuged to yield 162.4 grams of highly purified bisphenol-A. These crystals of bisphenol-A were further slurried with about 240 grams toluene, and again centrifuged to yield 159.02 grams highly purified crystalline bisphenol-A, the melting point of which was 155.5° C. indicating a high purity product. The mother and wash liquors in this test were collected and toluene was partially distilled (~70%) to give a total remaining weight of 418.8 grams of further BPA recovery. This mass, consisting of phenol, BPA, reaction by-product (isomers, etc.) and some toluene was slowly cooled to room temperature. Solids were observed to have formed upon cooling and were collected by the use of a high-speed centrifuge, whereupon the "secondary" mother liquor was removed. By this process 36.95 grams of additional solid BPA was collected. Analysis of the BPA product showed that it was 99.944% pure and that the recovery, based on the theoretical amount of bisphenol-A obtainable, was about 76.24%. The solid obtained from the "secondary" mother liquor was also analyzed and found that 78.27% of this was BPA and 20.73% was phenol indicating a recovery based on the theoretical amount of bisphenol-A possible of an additional 13.90%.

EXAMPLE 5

This example illustrates a process for using a mixture of toluene and water in obtaining the highly purified bisphenol-A. More particularly, 50.06 grams of the adduct, 100.04 grams water, and 99.96 grams toluene were placed in the reaction vessel described in Example 1 and stirred while heating to about 59° C. when all the solids disappeared, and a two liquid phase system was obtained with the organic layer on the top and the aqueous phase at the bottom. The system was slowly cooled and seed crystals of BPA were applied at a temperature of about 54.5° C. during the cooling process to induce crystallization. Upon cooling to 35° C., the stirring was discontinued to allow for phase separation by gravity. The top organic layer was removed and the remaining material (aqueous and solid phases) was poured into a Buchner funnel where liquid was separated from the solid. This yielded 29.95 grams of a solid material which was essentially pure bisphenol-A. This solid material was slurried with 45 grams of toluene, and after separation of the toluene and drying of the solid, 23.49 grams of pure bisphenol-A crystals were collected. These crystals had a melting point of 155°–156° C. Analysis of these crystals showed that they were 100% pure bisphenol-A and that percent recovery based on the theoretical amount of bisphenol-A was 67.8%.

It will of course be understood by those skilled in the art that in addition to the conditions and proportion of ingredients employed in the foregoing examples, other conditions of admixture, filtering, washing, and separating, ratios of the adduct to toluene, and toluene to water, and temperatures may be employed without departing from the scope of the intended invention more particularly described above.

What I claim as new and desire to secure by Letters Patent of the United States is:

1. The method of recovering 2,2-bis(4-hydroxyphenyl) propane in a purified state from a mixture of the latter and impurities therein derived from the acid condensation of phenol and acetone, which process comprises (1) combining a mixture of (a) a preformed isolated adduct of phenol and the above-identified dihydroxydiphenyl propane and (b) impurities associated with (a), with sufficient toluene alone or with a mixture of toluene and water to form a homogeneous solution with the toluene, or a liquid-liquid mixture when water and toluene are used, the toluene being employed, on a weight basis, from 0.5 to 10 parts toluene per part adduct, (2) heating the mixture at a temperature of from 45°–125° C., (3) cooling the solution or liquid-liquid mixture to a temperature where the aforesaid dihydroxydiphenyl propane precipitates in a highly purified state, and (4) isolating the purified 2,2-bis(4-hydroxyphenyl) propane.

2. The method as in claim 1 wherein the precipitated dihydroxy-diphenyl propane is washed with toluene or methylene chloride.

3. The method as in claim 1 wherein the toluene used is equal, by weight, from 0.5 to 10 parts toluene per part dihydroxydiphenyl propane.

4. The method as in claim 1 wherein the temperature of heating is from 45° to 110° C.

5. The process as in claim 3 wherein water is added to the toluene in an amount on a weight basis, equal to from 0.1 to 4 parts thereof per part toluene.

* * * * *